United States Patent

Jelich

Patent Number: 4,958,025
Date of Patent: Sep. 18, 1990

[54] PREPARATION OF 2-CHLORO-5-CHLOROMETHYLPYRIDINE

[75] Inventor: Klaus Jelich, Wuppertal, Fed. Rep. of Germany

[73] Assignee: Bayer Aktiengesellschaft, Leverkusen, Fed. Rep. of Germany

[21] Appl. No.: 445,816

[22] Filed: Dec. 4, 1989

[30] Foreign Application Priority Data

Dec. 16, 1988 [DE] Fed. Rep. of Germany ....... 3842358

[51] Int. Cl.$^5$ ............................................. C07D 213/61
[52] U.S. Cl. ................................................... 546/345
[58] Field of Search .......................................... 546/345

[56] References Cited

U.S. PATENT DOCUMENTS 4,634,771 1/1987 Shim .................................... 546/286

FOREIGN PATENT DOCUMENTS 0046653 3/1982 European Pat. Off. ............ 546/345
0072777 2/1983 European Pat. Off. ............ 546/345

OTHER PUBLICATIONS

Ziegler, Frederick, "Synthetic Studies . . . Yohimbine Alkaloids," J. Organic Chemistry, vol. 34, No. 11, pp. 3545–3548, Nov. 1969.

Primary Examiner—Mary C. Lee
Assistant Examiner—Jacqueline Haley
Attorney, Agent, or Firm—Sprung Horn Kramer & Woods

[57] ABSTRACT

A process for the preparation of 2-chloro-5-chloromethyl-pyridine of the formula

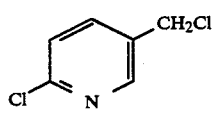 (I)

which comprises reacting nicotinic acid of the formula

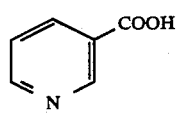 (II)

with phosphorus pentachloride to produce 3-trichloromethylpyridine of the formula

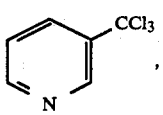 (III)

reacting the 3-trichloromethylpyridine in a 2nd step with an alkali metal alkoxide of the formula

R-O-M  (IV)

in which
R represents alkyl and
M represaents an alkali metal cation, to produce a pyridine ether acetal of the formula

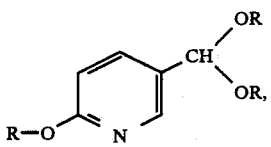 (V)

reacting the pyridine ether acetal in a 3rd step with dilute aqueous acid to produce pyridone aldehyde of the formula

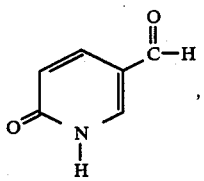 (VI)

hydrogenating the pyridone aldehyde in a 4th step with molecular hydrogen in the presence of a hydrogenation catalyst to produce the pyridylmethanol compound of the formula

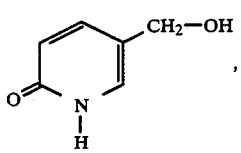 (VII)

and reducing the pyridylmethanol compound in a 5th step with a chlorinating agent.

2 Claims, No Drawings

PREPARATION OF 2-CHLORO-5-CHLOROMETHYLPYRIDINE

The invention relates to a new process for the preparation of 2-chloro-5-chloromethylpyridine, which is used as an intermediate for the preparation of known insecticides.

It is known that 2-chloro-5-chloromethylpyridine is obtained in a complicated, multi-step process when 2-chloropyridine-5-carboxylic acid is converted into the corresponding acid chloride using thionyl chloride, this acid chloride, if appropriate, is esterified with ethanol and subsequently reduced to give the hydroxymethyl compound using sodium boranate, and the hydroxyl group in the side chain is finally substituted by chlorine using thionyl chloride (cf., for example, U.S. Pat. No. 4,576,629; J. Org. Chem. 34, 3545 [1969]; J. Heterocycl. Chem. 16, 333–337 [1979]).

However, disadvantageous in this process and prohibitive for a large-scale industrial feasibility are the high costs of the starting compound 2-chloropyridine-5-carboxylic acid and of the reducing agent sodium boranate, which, additionally, presents a safety problem because of the evolution of hydrogen in the course of the reaction.

Furthermore, it is known that 2-chloro-5-chloromethylpyridine is obtained when 2-chloro-5-methylpyridine is reacted with elemental chlorine (cf., for example, DE-A 3,630,046). However, the disadvantage in this process is that the reaction does not proceed uniformly, which makes it necessary to disrupt the chlorination at an early point in time to avoid formation of substantial amounts of multichlorinated by-products, before the reaction could proceed to completion (cf. also EP-A 9,212; EP-A 65,358). The product mixtures formed can only be separated with difficulty and yield products of a purity which is unsatisfactory.

It has now been found that 2-chloro-5-chloromethylpyridine, of the formula (I),

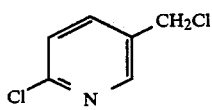

is obtained in high yield and high purity when, initially in a 1st step, nicotinic acid, of the formula (II),

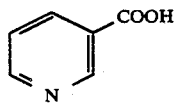

is reacted with phosphorus pentachloride, if appropriate in the presence of thionyl chloride and if appropriate in the presence of a diluent, the resulting 3-trichloromethylpyridine, of the formula (III),

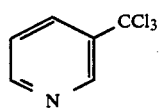

is then reacted, in a 2nd step, with alkali metal alkoxides of the formula (IV)

R-O-M  (IV)

in which
R represents alkyl and
M represents an alkali metal cation, if appropriate in the presence of a diluent, the resulting pyridine ether acetals of the formula (V)

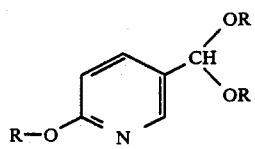

in which
R has the abovementioned meaning are then reacted in a 3rd step with dilute aqueous acid, the resulting pyridone aldehyde, of the formula (VI),

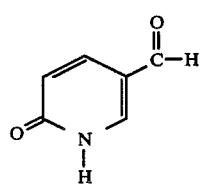

is then hydrogenated in the a step with molecular hydrogen in the presence of a hydrogenation catalyst and if appropriate in the presence of a diluent and the resulting pyridylmethanol compound, of the formula (VII),

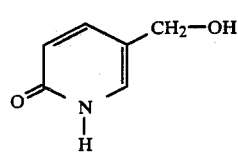

is finally reacted in a 5th step with a chlorinating agent, if appropriate in the presence of a diluent and if appropriate in the presence of a reaction auxiliary.

Steps 2 and 3 can also be carried out directly in one reaction step in the sense of a so-called one-pot process, without isolation of the intermediates.

The series of steps of the reaction sequence according to the invention is entirely surprising and not predictable by those skilled in the art.

Thus, for example, it could not be expected that the reaction of nicotinic acid with phosphorus pentachloride or with phosphorus pentachloride in the presence of thionyl chloride, respectively, according to step 1 of the process according to the invention would give 3-trichloromethylpyridine of the formula (III) in a smooth reaction and in very high yields, since, on the one hand, it was known from the prior art that phenylphosphine chlorides, which are highly reactive, complicated to prepare and difficult to handle, are required as chlorinating agents or reaction auxiliaries in order to achieve a higher yield (cf., in this context, US-A No. 4,634,771), and since, on the other hand, investigations by applicants and their colleagues revealed that the simple, direct reaction of nicotinic acid with phosphorus pentachloride (cf., in this context, Tetrahedron Letters 25, 5693–5696 [1984]) in substance and also in the presence of diluents only give yields of a maximum of 5% of desired trichloromethylpyridine compound of the formula (III).

The fact that the reaction of 5-hydroxymethyl-2-pyridone, of the formula (VII), with chlorinating agents, such as, for example, phosphorus oxychloride or phosgene, in accordance with step 5 of the process according to the invention would result in simultaneous exchange both of the hydroxyl group in the side chain and of the pyridone function in the 2-position of the pyridine system against one chlorine radical in each case, was likewise unexpected. A reaction of this type has not been known from the prior art to date.

Finally, a very particularly surprising aspect was the fact that the reaction of the pyridine ether acetals of the formula (V) with dilute aqueous acids in accordance with step 3 of the process according to the invention not only brings about a cleavage of the acetal group in the side chain, but simultaneously an ether cleavage in the 2-position of the pyridine ring takes place, even when the conditions are exceptionally mild, since it was known from the prior art that similar ether cleavages can only be carried out successfully under considerably more drastic reaction conditions, that is to say, using acids of a higher concentration and at higher temperatures (cf., for example, Organikum [Laboratory Practical in Organic Chemistry], VEB Deutscher Verlag der Wissenschaften Berlin 1981; pages 237, 244, 245, or J. Heterocycl. Chem. 10, 779, [1973]).

A particular advantage of the reaction sequence according to the invention which must be emphasized is that the starting substance nicotinic acid is an inexpensive starting material which can be prepared industrially on a large scale, and that moreover all reactions can be carried out with readily available reagents, under reaction conditions which can easily be established in industry, selectively and in high yield.

If, for example, nicotinic acid is used as the starting compound, thionyl chloride and phosphorus pentachloride as the reactants in step 1, sodium isobutoxide as the reactant in step 2, dilute hydrochloric acid as the reactant in step 3, Raney nickel as the hydrogenation catalyst in step 4, and phosgene in the presence of dibutylformamide as the chlorinating agent in step 5, the course of the reaction of the process according to the invention may be represented by the following equation:

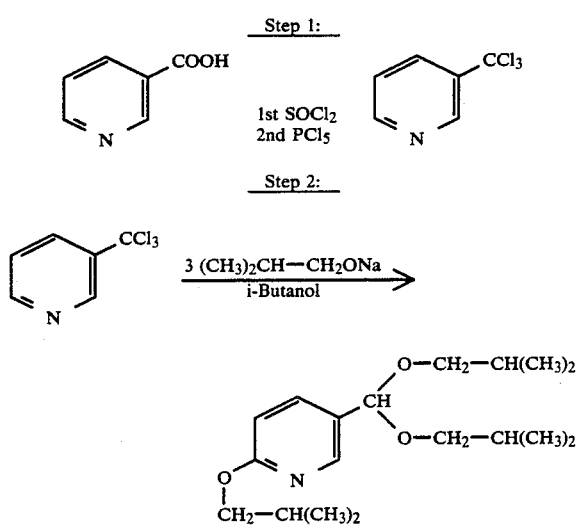

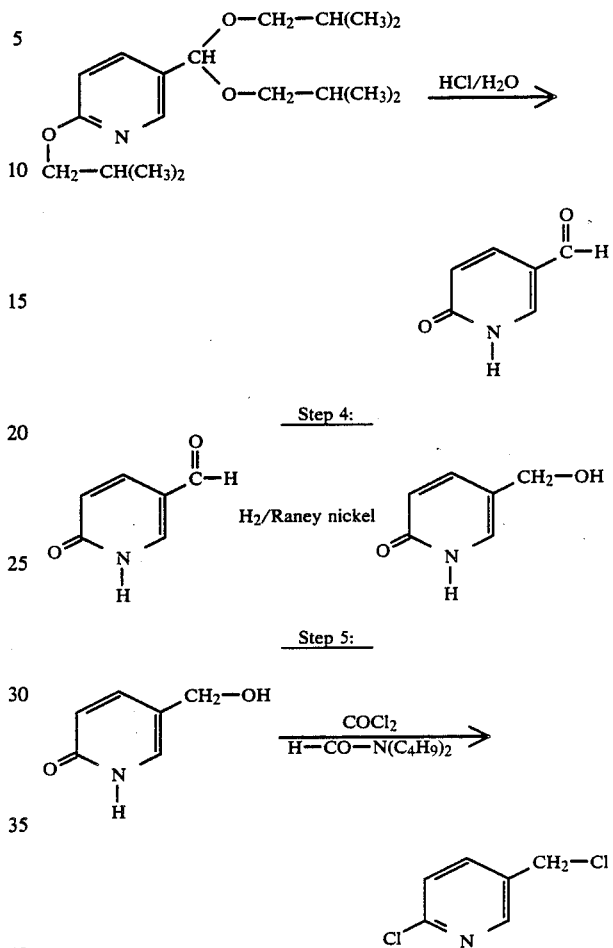

Suitable diluents for carrying out step 1 of the process according to the invention are inert organic solvents. Benzene, toluene, xylene, chlorobenzene, dichlorobenzene, nitrobenzene or phosphorus oxychloride are particularly preferably used. It is also possible to carry out step 1 of the process according to the invention directly, without using a diluent.

When carrying out step 1 of the process according to the invention, the reaction temperatures can be varied within a substantial range. In general, the process is carried out at temperatures between 80° C. and 180° C., preferably at temperatures between 110° C. and 160° C.

For carrying out step 1 of the process according to the invention, either 2 to 4 moles of phosphorus pentachloride or, in order to avoid a substantial excess of phosphorus pentachloride, initially 1 to 2 moles of thionyl chloride (in which process the starting substance nicotinic acid is converted into the hydrochloride of the corresponding acid chloride) and then 1 to 2 moles of phosphorus pentachloride are employed per mole of nicotinic acid, of the formula (II). It is also possible to prepare phosphorus pentachloride directly in the reaction vessel, from an appropriate amount of phosphorus trichloride and an equivalent amount of chlorine. In the course of the reaction, it is expedient to continuously distil off phosphorus oxychloride which has been evolved.

The reaction product of the formula (III) can be worked up and isolated by distillation; however, the crude product can also be employed directly for further reactions.

Formula (IV) provides a general definition of the alkali metal alkoxides required as starting substances for carrying out step 2 of the process according to the invention. In this formula (IV), R preferably represents a straight-chain or branched alkyl having 1 to 4 carbon atoms, in particular represents methyl, ethyl, isopropyl, i-butyl or sec-butyl. M preferably represents a sodium or potassium cation, in particular represents sodium.

The alkali metal alkoxides of the formula (IV) are generally known compounds; if required, they can be prepared in situ from alkali metal hydroxides and corresponding alkoxides.

Suitable diluents for carrying out step 2 of the process according to the invention are also inert organic solvents. Lower alkyl alcohols, which carry the same alkyl radical by which the alkali metal alkoxides of the formula (IV) to be used as reactants are characterized, in particular methanol, ethanol, isopropanol or isobutanol, are particularly preferably used.

When carrying out step 2 of the process according to the invention, the reaction temperatures can be varied within a substantial range. In general, the process is carried out at temperatures between 0° C. and 120° C., preferably at temperatures between 20° C. and 90° C.

For carrying out step 2 of the process according to the invention, 3.0 to 15.0 moles, preferably 3.5 to 6.0 moles, of alkali metal alkoxide of the formula (IV) are employed per mole of 3-trichloromethylpyridine, of the formula (III). The reaction is carried out and the reaction products are worked up and isolated by customary methods (cf. the Preparation Examples).

Suitable acids for carrying out step 3 of the process according to the invention preferably are dilute organic or inorganic protonic acids. Dilute aqueous hydrochloric acid, acetic acid, formic acid or sulphuric acid is preferably used as the reaction medium.

When carrying out step 3 of the process according to the invention, the reaction temperatures can be varied within a substantial range. In general, the process is carried out at temperatures between 20° C. and 120° C., preferably at temperatures between 50° C. and 100° C.

For carrying out step 3 of the process according to the invention, the pyridine ether acetals of the formula (V) are generally reacted in an 0.2 to 5.0% strength, in particular in an 0.5 to 1.0% strength, aqueous acid solution at the reaction temperature required. The reaction products are worked up and isolated by generally customary methods (cf. also the Preparation Examples).

Suitable hydrogenation catalysts for carrying out step 4 of the process according to the invention are customary noble metal catalysts, noble metal oxide catalysts or Raney catalysts, if appropriate on a suitable support, such as, for example, active carbon, alumina or silica. Palladium on active carbon or Raney nickel are particularly advantageously used.

Suitable diluents for carrying out step 4 of the process according to the invention are inert organic solvents. These in particular include ethers, such as diethyl ether, dioxane, tetrahydrofuran or ethyl glycol dimethyl ether or ethyl glycol diethyl ether, alcohols, such as methanol, ethanol, propanol, butanol, ethylene glycol monomethyl ether or ethylene glycol monoethyl ether, or acids, such as, for example, acetic acid.

When carrying out step 4 of the process according to the invention, the reaction temperatures can be varied within a substantial range. In general, the process is carried out at temperatures between 0° C. and 150° C., preferably at temperatures between 20° C. and 100° C.

Step 4 of the process according to the invention is preferably carried out under increased pressure. In general, the process is carried out in pressure ranges between 2 and 200 bar, preferably bet 10 and 100 bar.

For carrying out step 4 of the process according to the invention, 1.0 to 20.0 moles, preferably 1.0 to 5.0 moles, of hydrogen and 0.0001 to 1.0 mole, preferably 0.01 to 0.1 mole, of hydrogenation catalyst are generally employed per mole of pyridone aldehyde, of the formula (VI).

The reaction is carried out and the reaction products are worked up and isolated by generally customary methods (cf. also the Preparation Examples).

Suitable chlorinating agents for carrying out step 5 of the process according to the invention are, in particular, phosphorus pentachloride, phosphorus oxychloride or phosgene, as well as mixtures of these compounds.

Step 5 of the process according to the invention can be carried out either directly without the addition of a diluent, or in the presence of a suitable diluent. These include, in particular, aliphatic, alicyclic or aromatic, optionally halogenated hydrocarbons, such as, for example, benzene, toluene, xylene, chlorobenzene or dichlorobenzene, petroleum ether, hexane, cyclohexane, methylcyclohexane, dichloromethane, chloroform or carbon tetrachloride.

If appropriate, step 5 of the process according to the invention can be carried out in the presence of a suitable reaction auxiliary. Suitable reaction auxiliaries are tertiary amines, such as triethylamine, N,N-dimethylaniline, pyridine or N,N-dimethylaminopyridine, and additionally also catalytic amounts of formamides, such as, for example, N,N-dimethylformamide or N,N-dibutylformamide, or inorganic metal chlorides, such as magnesium chloride or lithium chloride.

When carrying out step 5 of the process according to the invention, the reaction temperatures can be varied within a substantial range. In general, the process is carried out at temperatures between 20° C. and 200° C., preferably at temperatures between 60° C. and 150° C.

For carrying out step 5 of the process according to the invention, 1.0 to 10.0 moles, preferably 1.0 to 5.0 moles, of chlorinating agent and if appropriate 0.01 to 3.0 moles, preferably 0.1 to 2.0 moles, of reaction auxiliary are generally employed per mole of pyridylmethanol, of the formula (VII).

The reaction is carried out and the reaction product of the formula (I) is worked up and isolated with the aid of known processes (cf. also the Preparation Examples). 2-Chloro-5-chloromethylpyridine, of the formula (I), is a known compound and can be obtained with the aid of the process according to the invention and employed, for example, as an intermediate for the preparation of insecticidal nitromethylene compounds (cf., for example, EP-A 163,855; EP-A 192,060; EP-A 259,738; EP-A 254,859).

PREPARATION EXAMPLES

Step 1:

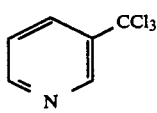

123.1 g (1 mol) of nicotinic acid are added in the course of 10 minutes to 250 ml of thionyl chloride, during which process the temperature of the mixture rises to 50° C. When the addition is complete, the mixture is stirred at 55° C. for 15 minutes, and excess thionyl chloride is then distilled off under reduced pressure. 275 g (2 mol) of phosphorus trichloride are then added, and a total of 140 g (2 mol) of dried chlorine gas is passed in in the course of 2 hours, during which process the temperature of the mixture rises to 70° C. After this, the mixture is heated for one hour at 150° C., during which process any phosphorus oxychloride which is evolved is continuously distilled off. For working up, the mixture is cooled, 600 ml of ethyl acetate are added, the mixture is poured into ice water and rendered weakly alkaline by adding sodium carbonate in portions and with cooling, the organic phase is separated off, and the aqueous phase is extracted using 300 ml of ethyl acetate. The combined organic phases are dried over magnesium sulphate, concentrated in vacuo and distilled under a waterpump vacuum.

176.8 g (89% of theory) of 3-trichloromethylpyridine of boiling point 105° C.-107° C. at 15 mbar are obtained.

Step 2:

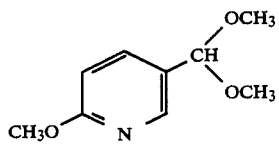

31.6 g (0.161 mol) of 3-trichloromethylpyridine are added dropwise and with stirring in the course of 45 minutes at reflux temperature to 140.7 g (0.515 mol) of a solution of sodium methoxide in methanol. When the addition is complete, the mixture is stirred for 3 more hours at reflux temperature and then cooled and filtered, the filtrate is concentrated, the residue is taken up in dichloromethane, the mixture is filtered once again, the filtrate is concentrated, and the residue is distilled in vacuo.

24.5 g (83% of theory) of 2-methoxy-5-bis-(methoxy)-methyl-pyridine of boiling point 54° C.-55° C. at 0.25 mbar are obtained.

Step 3:

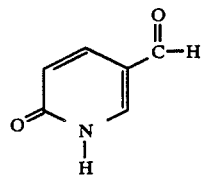

41.5 g (0.227 mol) of 2-methoxy-5-bis-(methoxy)-methyl-pyridine are refluxed for 3 hours in 300 ml of 0.5% strength aqueous hydrochloric acid, the mixture is subsequently concentrated to a volume of about 120 ml and cooled to 0° C., and the solid which has precipitated is filtered off with suction and dried.

22.5 g (81% of theory) of 2-pyridinone-5-aldehyde of melting point 222° C. are obtained.

Step 4:

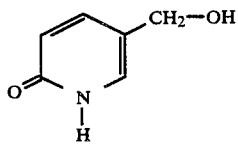

2 g of Raney nickel are added to 10.0 g (0.081 mol) of 2-pyridinone-5-aldehyde in 200 ml of ethanol, and the mixture is subsequently hydrogenated for 4 hours at 80° C. and 30 bar hydrogen pressure. For working up, the catalyst is filtered off, the filtrate is concentrated, and the solid which remains is purified by stirring with ethyl acetate, filtering off with suction and dried.

7 g (78% of theory) of 5-hydroxymethyl-2-pyridinone of melting point 130° C. are obtained.

Step 5

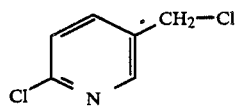

2.0 g (0.016 mol) of 5-hydroxymethyl-2-pyridinone are added to a mixture of 6.7 g (0.032 mol) of phosphorus pentachloride and 2.5 g (0.016 mol) of phosphorus oxychloride, the mixture is stirred at reflux temperature for 7 hours, cooled and taken up in ethyl acetate, ice water is then added, the mixture is rendered neutral using sodium carbonate, the organic phase is separated off and dried over magnesium sulphate, and the solvent is removed under reduced pressure. The residue may be purified by distillation.

2.5 g (96% of theory) of 2-chloro-5-chloromethyl-pyridine of boiling point 70° C.-80° C. at 1 mbar are obtained.

It will be appreciated that the instant specification and claims are set forth by way of illustration and not limitation, and that various modifications and changes may be made without departing from the spirit and scope of the present invention.

What is claimed is:

1. A process for the preparation of 2-chloro-5-chloromethyl-pyridine of the formula

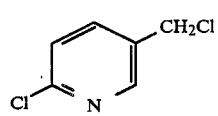

(I)

which comprises reacting nicotinic acid of the formula

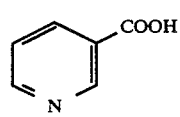

(II)

with phosphorus pentachloride to produce 3-trichloromethylpyridine of the formula

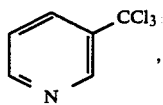 (III)

reacting the 3-trichloromethylpyridine in a 2nd step with an alkali metal alkoxide of the formula

R-O-M (IV)

in which
R represents alkyl and
M represents an alkali metal cation, to produce a pyridine ether acetal of the formula

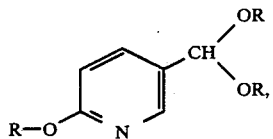 (V)

reacting the pyridine ether acetal in a 3rd step with dilute aqueous acid to produce pyridone aldehyde of the formula

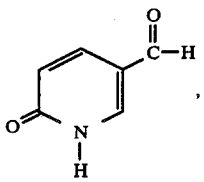 (VI)

hydrogenating the pyridone aldehyde in a 4th step with molecular hydrogen in the presence of a hydrogenation catalyst to produce the pyridylmethanol compound of the formula

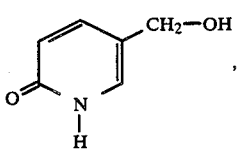 (VII)

and reducing the pyridylmethanol compound in a 5th step with a chlorinating agent.

2. A process according to claim 1, wherein the 2nd and 3rd steps are carried out without isolation of the intermediates.

* * * * *